United States Patent
Khudenko

(10) Patent No.: US 6,984,323 B2
(45) Date of Patent: Jan. 10, 2006

(54) BIOLOGICAL TREATMENT PROCESS

(76) Inventor: Boris M. Khudenko, 744 Moores Mill Rd., Atlanta, GA (US) 30327

( * ) Notice: Subject to any disclaimer, the term of this patent is extended or adjusted under 35 U.S.C. 154(b) by 0 days.

(21) Appl. No.: 10/010,271

(22) Filed: Nov. 5, 2001

(65) Prior Publication Data

US 2003/0085171 A1 May 8, 2003

(51) Int. Cl.
C02F 3/30 (2006.01)

(52) U.S. Cl. ............... 210/603; 210/605; 210/610; 210/631; 210/903; 210/906

(58) Field of Classification Search ............ 210/603, 210/605, 620, 621, 622, 631, 610, 903, 906
See application file for complete search history.

(56) References Cited

U.S. PATENT DOCUMENTS

| | | | | |
|---|---|---|---|---|
| 4,568,457 A | * | 2/1986 | Sullivan | 210/151 |
| 5,702,604 A | * | 12/1997 | Yamasaki et al. | 210/603 |
| 5,846,424 A | * | 12/1998 | Khudenko | 210/603 |
| 6,015,496 A | * | 1/2000 | Khudenko | 210/603 |
| 6,063,273 A | * | 5/2000 | Habets et al. | 210/188 |

FOREIGN PATENT DOCUMENTS

JP           60-235698         * 11/1985

* cited by examiner

Primary Examiner—Fred G. Prince

(57) ABSTRACT

This is a method of waste treatment in tall reactors having with anaerobic biological stage in the lower section of the reactor and another treatment stage in the upper section of the reactor, these stages are separated by an essentially horizontal partition. Presurized digestion gases generated in the anaerobic section are collected under the partition. The process is further improved by providing a recuperable alkalinity and stripping of biologically generated carbon dioxide. so that the free carbon dioxide concentratiooon in the anaerobic mixed liquor is very low and a methane-rich digestion gas is produced. Production of pressurized methane-rich digestion gas is the major benefit of the process. Ather improvements are in the controllable gaslift mixing with gases other than digestion gases, improved process performance with increasing operating temperatures due to bioheating, and improved solid-liquid separation due to the use of the distillation techniques making use of the bioheating and heat recycle.

20 Claims, 8 Drawing Sheets

BIOLOGICAL TREATMENT PROCESS

FIELD OF INVENTION

This invention relates to anaerobic and anaerobic-aerobic processes conducted in stacked sections, and particularly concerned with mixing, separation and collection of digestion gases, generation of methane-rich digestion gases, and solid-liquid separation in stacked reactors.

PRIOR ART

A stacked two-stage anaerobic reactor for treatment of liquid wastewater have been disclosed by Vellinga in U.S. Pat. No. 4,609,460, stacked anaerobic-aerobic reactors for treatment of liquid wastewater and for considerably viscous wastewater sludges have been disclosed by Khudenko in U.S. Pat. Nos. 5,514,277 and 5,616,241, and by Habets et. al. in U.S. Pat. Nos. 5,972,219 and 6,063,273. The described methods and apparatus address passive mixing of liquid wastewater by digestion gases and separation of the treated liquid from the sludge due to gravity in fluidized beds with garnular sludge and in quiescent settling devises as commonly used for liquid wastewater. Khudenko also teaches how to produce digestion gas substantially free from hydrogen sulfide. Passive mixing in fluidized beds are described by Khudenko in U.S. Pat. No. 4,472,358, by Vellinga in U.S. Pat. No. 4,609,460, and by Habets in U.S. Pat. No. 6,03,273. Passive mixing of viscous sludges is described in by Khudenko in U.S. Pat. No. 4,472,358 and by Edwards in U.S. Pat. No. 5,441,634. Active mixing in fluidized beds by recycling effluent with pumps is well known. The problems of such recycling are as follows: it is very difficult to produce uniform or other predetermined distribution of flows with multiple suction ports and a single pump or a single header and several pumps, use of multiple pumps is complex, it is difficult to select pumps with very low head as needed for most mixing applications because such pumps are not made, pipelines are large and require many turns, many control valves are required, electrical part for the system of many pumps becomes complex, sludge flocks and granules break up in pumps and pipelines with multiple turns. Active mixing with various submersible propeller mixers is also known. Propeller mixers have problems similar to those of pumps. One active system of airlift-mixers for fluidized beds is described by Khudenko in U.S. Pat. No. 6,048,459 and for fluidized beds and viscous sludges in a co-pending patent application. A method of providing pH and alkalinity control with an additional benefit of generating methane-rich digestion gas virtually free from hydrogen sulfide is described by Khudenko in U.S. Pat. No. 5,798,043. None of these technologies provides for collection of treated methane-rich digestion gas under pressure, an option that would greately improve conditions for utilization of this gas instead of flaring it. Collection of the digestion gas can be further improved if the reactors are made taller. Above-ground reactors, or conventional at least partially in-ground reactors are usually limited in height by about 25 meters, and sometimes somewhat taller.

U.S. Pat. Nos. 4,217,211, 4,251,361, 4,253,949, 4,287,070, 4,374,027, 4,466,928, 4,477,393, 5,503,748, 5,650,070, 5,651,892, 5,645,726, 5,660,724, 6,214,228 B1, Re. 30,944 describe a variety of aerobic and otherwise aerated treatment systems making use of airlift-aerators for the combined purposes of aerating and mixing. These systems have an advantage of a very deep reactor of up to 150–200 meters deep. Such system can be very economical for conducting thermophilic processes, which present great advantages in both the process rate and the degree of treatment. The use of combined anaerobic-aerobic systems, especially with sludges of both anaerobic and aerobic steps being at least partially mixed further significantly improves the performance.

Accordingly, the main objective of the present invention is to provide a stacked anaerobic-aerobic process with active controllable mixing of either fluidized beds or viscous sludges in reactors.

Another objective of the present invention is to generate and collect under pressure a methane-rich clean digestion gas.

Another objective of the present invention is to provide a simple and economical way of separating solids and liquid in treatment processes, while increasing a quality of the effluent and improving the biological processes in reactors.

Yet another objective of the present invention is to increase the biological process rate and degree of treatment.

Other objectives will become apparent from the ensuing description of the invention.

SUMMARY OF INVENTION

This is a method of biological treatment of wastewater with biomass. Wastewater and biomass form mixed liquor. Preferably, a tall reactor is used, for example, predominantly in-ground deep shaft reactor, or above ground column type reactors of a substantial height, much greater than conventional 3–4.5 m. The reactor has a closed or open top, a bottom, and an essentially horizontal partition between the top and the bottom. Depending on the technological (treatment related) and structural requirements, the partition can be flat, conical, pyramidal, or curvilinear, convex or concave, or of other shape. The main process steps comprise (a) at least one anaerobic treatment step conducted between the bottom and the partition, a digestion gas comprising methane and carbon dioxide is formed in the anaerobic treatment, (b) a step of mixing said mixed liquor in said anaerobic step by at least one controllable gaslift with a gas other than the digestion gas. At least one step of treatment of wastewater can be conducted between the partition and top of said reactor. The organic loaded waste can be water, wastewater, wastewater sludge, hazardous waste, manure, guano, industrial waste, agricultural waste, polluted soils, contents of polluted ponds and lagoons, and combinations thereof. These mixing steps are very effective not only for treatment of wastewater with dilute biomass but also for treatment of thicker sludges or wastewater with high content of biomass. This method is also more convenient than mixing with digestion gases: there is no corrosion of equipment by digestion gas impurities, no gas leak and fire problems. Unlike with other mixing systems, critical equipment (everything but the submerged pipes) can be open to the atmosphere and is easy to operate, repair, and replace.

The controllable gaslift lifts the mixed liquor from at least one location between the bottom and the partition to the uppermost point of said controllable gaslift and returns said mixed liquor in said anaerobic treatment step. The lifting and returning constitute a lifting-returning operation step effecting said mixing. Usually, the most convenient uppermost point of the gaslift is above the top of the reactor. However, this point can be at any elevation from the intake or discharge level of the gaslift, whichever is higher, to the top of the reactor. The lifting-returning operation step can include a nonreversible flow in airlift pipes, reversible flow, when the same pipe is used, first, to lift liquid and than to return it back, continuous flow meaning a constant flow rate all the time, discontinuous flow, a flow through a riser-downcomer pipe, a flow through a system of stacked contracting-expanding zones, for example stacked cones forming a virtual pipe which is a nonconfined hydraulic stream within the liquid volume, periodic flow, for example on/off flow or stepwise changing flow, and combinations thereof. Gas other than the digestion gas can be an oxidizing gas, oxygen, air, oxides of nitrogen, nitrogen, and combinations thereof. The oxidizing gas provides oxidizing reactions in the mixed liquor, whereby the mixed liquor is heated. The oxidizing reactions can be biological reactions, abiotic reactions, and combinations thereof.

Stripping carbon dioxide from the mixed liquor in the anaerobic treatment step can also be provided. Stripping carbon dioxide can be done by gas stripping, oxygen stripping, air stripping, nitrogen stripping, steam stripping, vacuum-stripping, vacuum-vapor-stripping, vacuum-vapor-stripping with steam recompression and condensation, vacuum-vapor-stripping with steam recompression and condensation with preheating the influent, vacuum-vapor-stripping with steam recompression and condensation with heating the contents of said reactor, heat degassing, and combinations thereof.

The method also provides steps of vaporization of wastewater from the mixed liquor with production of a low pressure steam. This steam is condensed and becomes the treated effluent. The vaporization method can be vaporization by preheating the mixed liquor, vaporization by vacuuming the mixed liquor, vaporization by vacuuming the mixed liquor with steam recompression and condensation, vaporization by vacuuming the mixed liquor with steam recompression and condensation and preheating the influent, vaporization by vacuuming the mixed liquor with steam recompression and condensation and preheating the mixed liquor, and combinations thereof.

The method also provides steps of feeding reagents, for example, recuperable alkaline species, recuperable oxidation-reduction species, alkalies, acids, nutrients, micronutrients, probiotics, and combinations thereof. Recuperable alkaline species help to control pH and alkalinity by creating a carbonate-bicarbonate buffer which is maintained by stripping biologically produced carbon dioxide. Calcium and iron ions are most practicable species. The bulk of these metals is in form of insoluble carbonates or hydroxides at the stage of solid-liquid separation. Recuperable oxidation-reduction species mediate oxidation-reduction of the original organics in the wastewater, intermediate products and the sludge. Iron ions are most practicable oxidation reduction species. They cycle between ferric and ferrous ions, ferric ions are made of ferrous by oxidation with oxygen, nitrates and nitrites, some halogenated organics, and some other species. The bulk of these ions is in form of insoluble hydroxides at the stage of solid-liquid separation. Maintaining elevated alkalinity also produces very low carbon dioxide concentration in the anaerobic mixed liquor. Accordingly, very high methane content of the harvested digestion gas can be obtained.

The method also provides for transferring the mixed liquor between anaerobic and other process steps. Additionally, the partition can be a flow-through means capable of collecting the digestion gas and passing through the mixed liquor, or at least partially clarified water. The step of treatment of said wastewater conducted between the partition and the top of the reactor can be an aerobic treatment, an aerobic treatment with aeration by air, an aerobic treatment with aeration by oxygen, an aerobic treatment with nitrification, an aerobic treatment with denitrification, an aerobic treatment with phosphorus removal, an anoxic treatment, a treatment with iron as an intermediate oxidation-reduction specie, an anaerobic hydrolysis treatment, an anaerobic acetogenic treatment, an anaerobic acidogenic treatment, an anaerobic sulfate reduction treatment, an anaerobic methanogenic treatmentg, and combinations thereof.

This is also a method of biological treatment of wastewater with biomass, where wastewater and biomass form mixed liquor. Tall reactors are preferably used. The reactor has a top, a bottom, and an essentially horizontal partition between said top and said bottom. The main process steps comprise (a) at least one anaerobic treatment step conducted between said bottom and said partition, a digestion gas comprising methane and carbon dioxide is formed in such anaerobic treatment, (c) at least one step of treatment of wastewater conducted between the partition and the top of the reactor, and (d) collecting digestion gas under the partition, whereby the collected gas is pressurized. The accumulation and the release of the gas from under the partition are controlled such a way that the gas volume under the partition changes between preset maximum and minimum values. This simple task can be performed by a variety of ways well familiar to skilled in art. This process modification can also include step of stripping carbon dioxide from the mixed liquor in the anaerobic treatment step. Stripping can be coupled with maintaining high alkalinity. As previously described, a methane-rich digestion gas results. Collecting methane-rich digestion gas under pressure can reduce the gasholder requirements by an order of magnitede, while doubling or tripling the heat value of the gas. Moreover, this gas is also free from hydrogen sulfide. Accordingly, the gas quality and the convenience of the gas storage greatly increase, thus making the gas utilization (instead of flaring) a very attractive option.

This is further a method of biological treatment of wastewater with biomass, where wastewater and the biomass form mixed liquor, in a tall reactor, said reactor having a top, a bottom, and an essentially horizontal partition between the top and the bottom, comprising (a) at least one anaerobic treatment step conducted between the bottom and the partition, a digestion gas comprising methane and carbon dioxide is formed in the anaerobic treatment, (c) at least one step of treatment conducted between the partition and the top of the reactor, and (e) at least one step of vaporization-separation of liquid from solids in said mixed liquor, whereby the separated liquid constitutes the treated effluent. The step of vaporization can be vaporization by preheating the mixed liquor, vaporization by bioheating the mixed liquor, vaporization by vacuuming the mixed liquor, vaporization by vacuuming the mixed liquor with steam recompression and condensation, vaporization by vacuuming the mixed liquor with steam recompression and condensation and preheating the influent, vaporization by vacuuming the mixed liquor with steam recompression and condensation and preheating the mixed liquor, and combinations thereof. The bioheating is provided by oxidizing the organics and the biomass with an oxidizer such as oxygen of air, oxygen, iron as intermediate oxidation-reduction specie, and combinations thereof. The method further provides a step of vacuum evacuation of digestion gases from mixed liquor simultaneously with step (e). The of vacuum evacuation of gases can be chemical vacuum evacuation, steam recompression vacuum evacuation, and combinations thereof. Chemical evacuation involves absorption with chemical reaction, for example, absorption of carbon dioxide into an alkaline solution. Steam recompression is a process used mainly in water distillation. It involves a vacuum-compressor (a blower) which pumps water vapors through with a vacuum at the suction side and some pressure at the discharge side. In the present case, the vacuum compressor will pull in under vacuum both, the water vapors and the gases. On the discharge side, water vapor is condensed while gases are separated from water and evacuated for utilization or discharge.

The method taught in this application can be carried out in a reactor selected from the group of deep shaft reactors, tall above-ground reactors, multi-cell reactors, and combinations thereof. Deep shaft reactors can be as deep as 150–200 m, above ground tanks are from at least 5 to 25 m and possibly taller. Multi-cell tanks are a considerably large footprint reservoirs divided into smaller cells to take advantage of the hydraulics of tall tanks. Either both, the bottom and the top sections or only bottom, or only top sections of multi-cell tank can be divided into cells. Top and bottom cells may also have different dimensions.

DRAWINGS

DETAILED DESCRIPTION OF EMBODIMENTS

Figure 1:
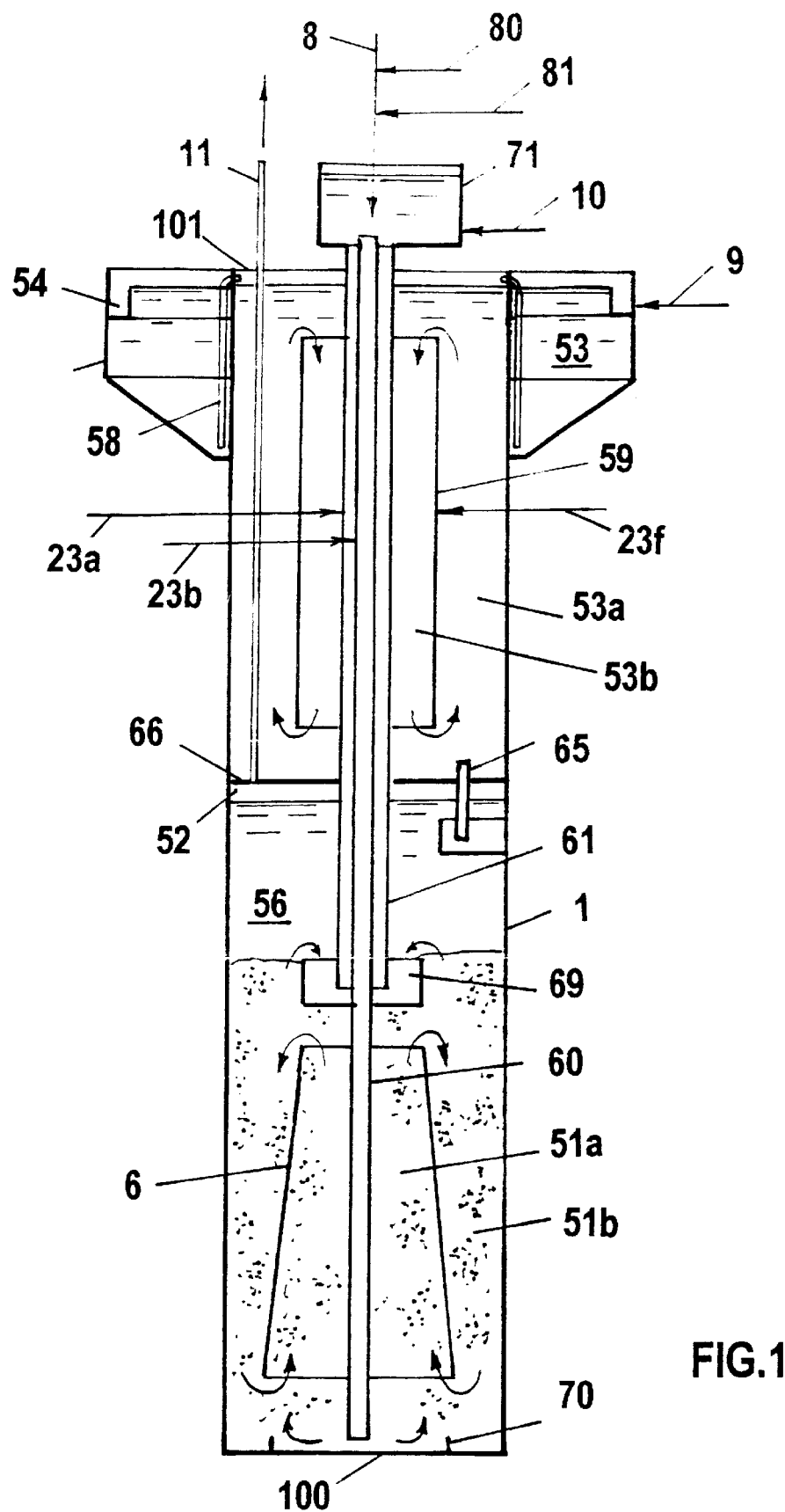
FIG. 1 is a stacked reactor with anaerobic stage at the bottom and aeated stage at the top, the reactor is provided with passive and active mixing means and with a pressurized digestion gas collection.

Referring now to FIG. 1, there is shown a reactor 1 having a bottom 100, a top 101, and a partition 66 defining the bottom anaerobic section comprising zones 51a and 51b, 56, and 52 respectively for reaction, at least partial sludge separation, and gas collection. A mixing cone 6 is a passive mixing means. Pipelines 60 and 61 with air (or oxygen, or another nondigestion gas) supply lines 23a and 23b connected to an elevated vessel 71 are the active mixing means. Optionally, vessel 71 is provided with an air line 10 and distributors (not shown) for stripping carbon dioxide. Also optionally, an influent line 8 and lines for feeding reagents 80 (for example, for lime) and 81 (for example, for iron) are connected to vessel 71. Alternatively, lines 8, 80, and 81 can be connected to the anaerobic process stage, or to the aerated process stage. A calming box 69 is provided at the lower end of pipeline 61, and flow directors 70 are provided around the lower end of pipeline 60. The gas collection section 52 is provided with a line 11 for gas evacuation. A flow passage 65 across the partition 66 with a flow calmer is provided. A central pipe 59 and an air (or oxygen) line 23f are provided in the upper aerated stage 53a. The upper stage also has a circular clarifier 55 with an effluent collection flume 54, sludge return airlifts 58, and an effluent line 9. Optionally, means for conveying anaerobic mixed liquor to the aerated stage and for feeding mixed liquor from the aerated stage to the anaerobic stage can also be provided. These mixed liquor transfer means are not shown in FIG. 1.

The embodiment of FIG. 1 is operated as follows. The influent via line 8 is fed in vessel 71 and ultimately, via line 60 or 61 in the anaerobic process stage wherein it undergoes anaerobic transformations resulting in organics conversion to water, carbon dioxide, methane, and lesser quantities of ammonia and hydrogen sulfide. The process is intensified by mixing. Mixing is naturally provided by the digestion gas, however, the quantity of gas per unit volume of the reactor diminishes with increased degree of treatment, and additional mixing is required. Mixing can be partially intensified by using a cone 6 which produces circulations as shown in FIG. 1 and as described in the U.S. Pat. No. 4,472,358 which is made a part of this application by inclusion. Lacking a generic term, the term cone is used here in a broad sense. Actually, it can be a pyramid, or a pair of oppositely inclined baffles forming a contracting cross section in the direction of the flow, or other shape producing effect of flow contraction and circulation around baffles. Such cones may not provide sufficient mixing, especially at low gas production rates. Accordingly, active mixing means should be used. A simple version of such means is as follows: air is fed via line 23a in pipeline 61 and lifts liquid from the calming box 69 and ultimately from the top of fluidized bed or from the upper part of the viscous sludge in the vessel 71. From vessel 71 thus lifted liquid descends via pipe 60 to the reactor bottom 100, strikes the bottom, and the flow directors 70 and flows upwardly. If the cone 6 is present, the flow forms the rotational patterns as shown by arrows. Alternative patterns of mixing streams can be produced by skilled in arts, for example, a rotational bottom flow as in the U.S. Pat. No. 5,338,447, or other, preferably nonuniform flows. The digestion gas accumulates in the liquid and separates into bubbles, which flow up and become collected in section 56 from where the gas is evacuated via line 11. Unlike in other systems, digestion gas is evacuated under substantial pressure thus saving on the compression equipment and storage volumes. This is an important unexpected benefit. Another unexpected benefit is in the use of air in the active airlift which produces stripping of carbon dioxide and thus greatly improves pH and alkalinity control in the system. This effect is further improved by stripping carbon dioxide by air (or oxygen) fed via line 10 in vessel 71. The stripping process is additionally improved by providing recuperable alkaline species, calcium and iron, as described in the U.S. Pat. No. 5,798,043 which is made a part of the present invention by inclusion. It may be important to strip carbon dioxide from largely bicarbonate solution by forming carbonates of calcium provided with lime or otherwise. When calcium carbonate is formed, it is precipitated in the biomass. When this biomass is returned in the anaerobic stage, thus precipitated carbonate reacts with carbon dioxide and makes bicarbonates. Accordingly, pH in the reactor is not significantly reduced and carbon dioxide gas is not released from the solution. Hence, only methane-rich gas is released. It is important that the total amount of the carbonate alkalinity and the rate of recycle of this alkalinity are sufficient to substantially exclude free carbon dioxide formation.

Another benefit is in bioheating of the wastewater or sludge due to oxidation by oxygen of air or better by oxygen in the airlift line 61 and in the stripping step conducted in vessel 71. Such heating increases the process rate. The aerated section is operated as usual aeration tank with aerators or with airlift-aerators. Aerated stage can be either a conventional activated sludge process, or process with nitrification, or a microaeration process, or any other process with various levels of oxidation-reduction potentials. Moreover, even methanogenic bacteria can be provided in the aerated stage, these bacteria producing methane. Airlift-aerators are shown in FIG. 1. As described in prior art, airlift-aerators have a partially aerated downcomer and aerated riser. In case of using oxygen instead of air, virtually all oxygen can be absorbed and consumed in the process thus reducing the quantity of off gases and heat loss with off gases and improving the heating efficiency of the process overall. The absorbtion of gases can be further increased by providing iron ions in the reactor. In aerated stage, iron in ferrous form is oxidized to ferric ions by oxygen and thus increases oxygen absorbtion via chemosorbtion mechanism, with ferric ions oxidizing organics and sludge in the system. Ferric and ferrous ions also participate in oxidation-reduction removal of ammonia and nitrates and nitrites with the formation of nitrogen. The beneficial effects of iron ions are described in U.S. Pat. No. 5,919,367 which is made a part of this application by inclusion. For many waste the present invention may increase the total methane content in the digestion gas from about 50% to 95%, and the collected gas pressure may be several atmospheres, for example, 3 ata. At such conditions, the volume of the required gas storage may be reduced almost by a factor of six. This is a very tangible benefit for many industries and municipalities.

Alternative operations of the active airlift system may include using only line 60 in a reciprocal regime: when vessel 71 is filled via line 60, air in line 23b is shut off and flow goes from the vessel 71 to the reactor bottom. Another alternative can be when one or both airlifts can be operated periodically, both airlifts can be operated in a reciprocal flow regime, line 60 can be a riser and line 61 can be a downcomer, lines 60 and 61 can be alternating in the riser-downcoming regimes. Such mixing in multiple points with very variable operating regimes is virtually impossible with pumps and submersible mixers. Additionally, airlifts have no moving parts, easy to service (only air solenoids beyond the reactor volume), and are unlikely to break down, if well made. Even best pumps and especially submersible mixers periodically break down, require extraction from the system for service and repair.

Figure 2:
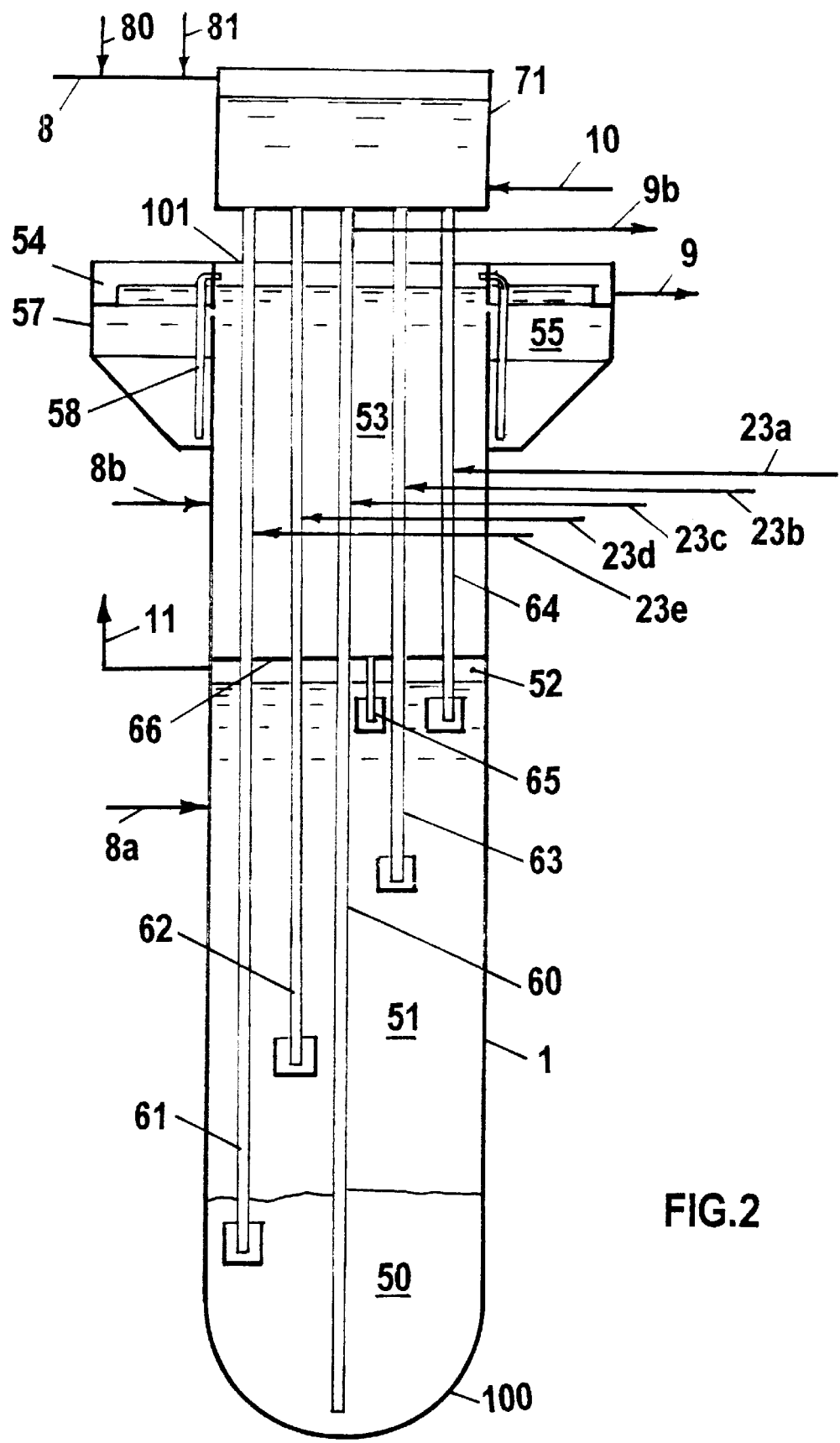
FIG. 2 is an alternative embodiment of FIG. 1 having multiple active gaslift means.

Referring now to FIG. 2, there is shown a modified version of the reactor of FIG. 1. The common parts of these reactors will not be described. FIG. 2 shows alternative feed locations 8a and 8b for the influent directed in the aerated stage and in the anaerobic stage respectively. The reactor 1 has a curvilinear bottom 100, there are no mixing cones in the anaerobic section and there is no airlift aerators in the aerated stage. The anaerobic stage is provided with multiple gaslifts 60, 61, 62, 63, and 64 having intakes at various elevations and terminating in the vessel 71. These gaslifts can be operated periodically, for example, gaslift 60 can periodically lift some well digested methanogen-rich sludge from the reactor bottom, this sludge can be fed down any of the remaining airlifts and mixed with the sludge volume being digested. In such a case, the bottom part of the reactor will serve as a sludge conditioner as described in U.S. Pat. No. 5,514,277. This patent is made a part of the present application by inclusion. The contents of any vertical segment between intakes of the gaslifts of the anaerobic stage can be mixed with any other segment or recycled from the bottom up or in opposite direction within any segment. Gaslifts may be provided with a variable flow of air so that at a lower air feed the gaslift stays in a neutral position, which means it does not lift any noticeable quantity of liquid and does not let any noticeable quantity to flow down. At maximum air feed, the gaslift lifts the liquid in the vessel 71. When air is not fed, the gaslift becomes a downcomer. Additionally, the vessel 71 can be split into more than one compartment. More than one gaslift originating at a given elevation in the reactor can be provided. Such arrangements of active mixing can be very convenient and effective in anaerobic deep shaft reactors or deeper anaerobic reactors. The use of air and/or oxygen will provide the benefits already discussed in the FIG. 1. The aerated stage can be operated as previously described with the airlift-aerator or as a more conventional aerated stage.

Figure 3:
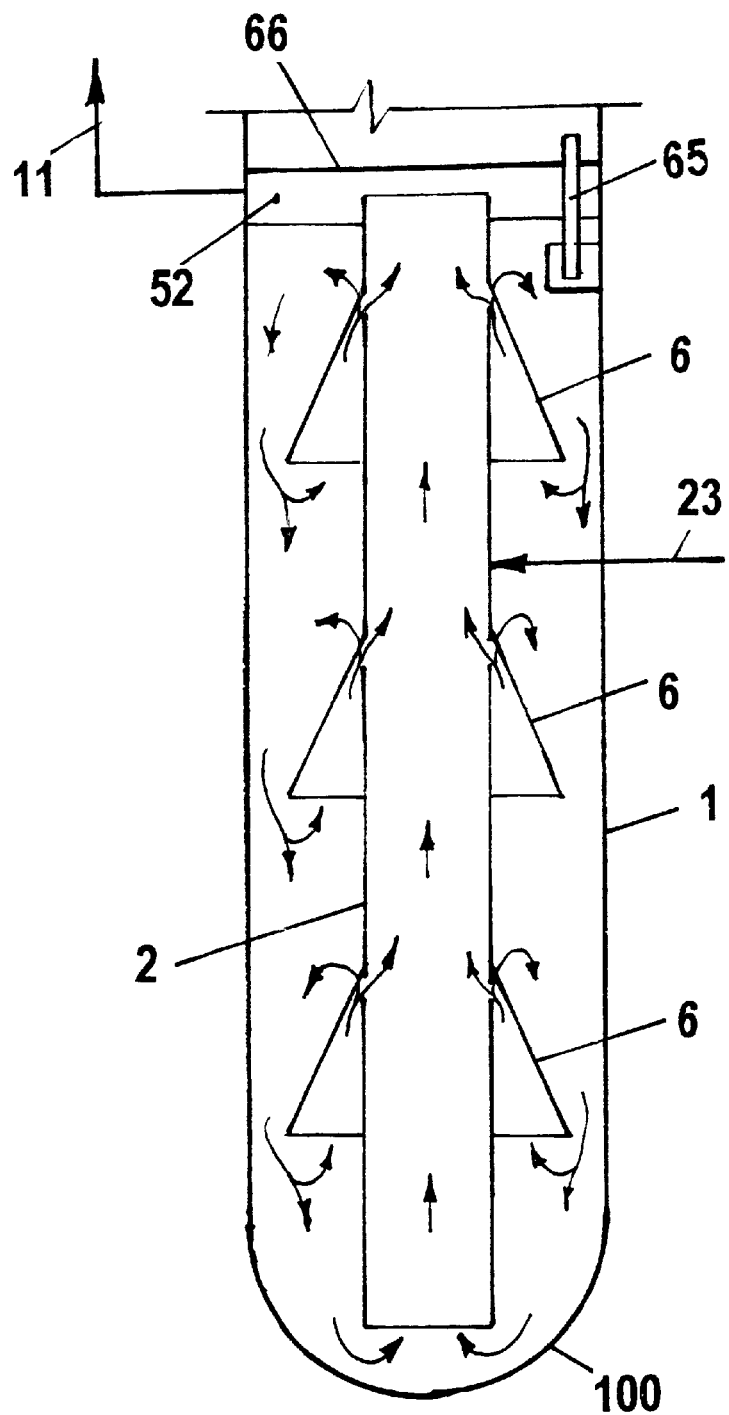
FIG. 3 is a bottom section of anaerobic reactor showing a passive means for sludge or fluidized bed mixing and active means in form of a pipe-gaslift with complete absoption of the driving gas.
Figure 4:
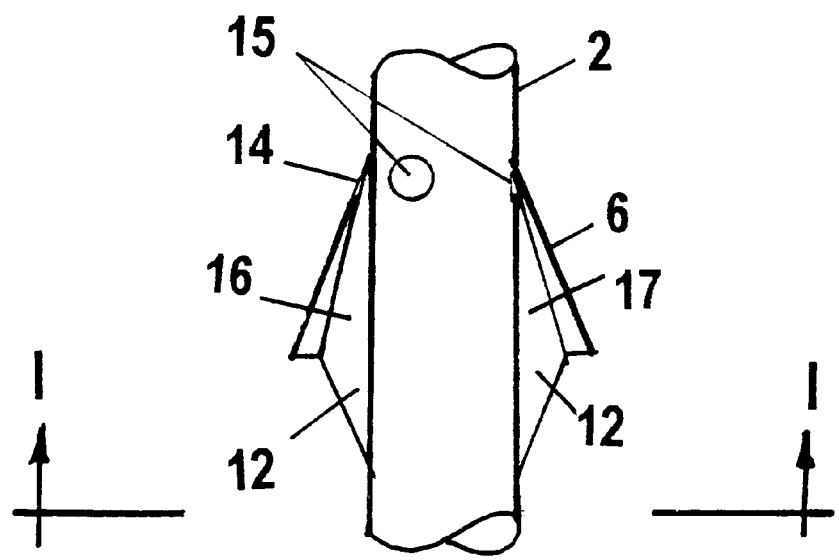
FIGS. 4 and 5 are details of the improved passive mixing system.
Figure 5:
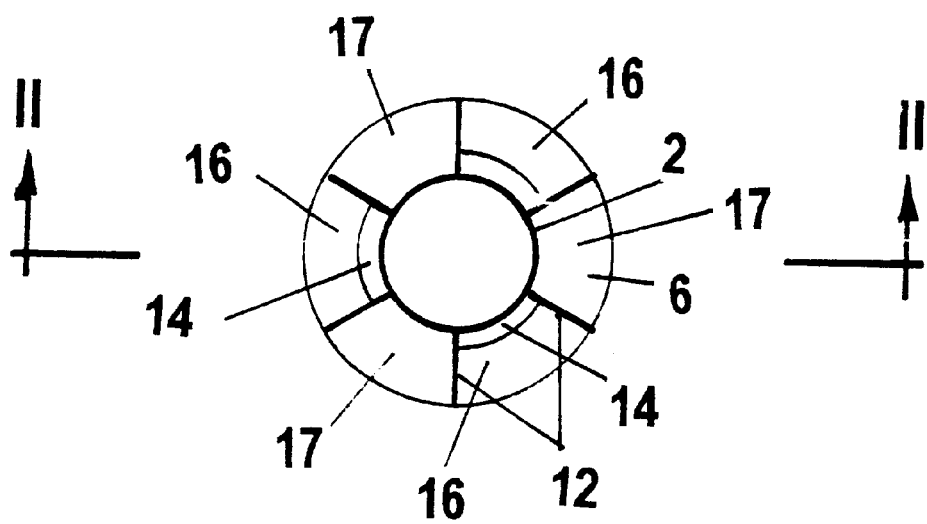

Referring now to FIGS. 3, 4, and 5 there is shown an anaerobic stage of the reactor 1 from the bottom 100 to the partition 66. The upper stage is not shown. It can be the same as in FIGS. 1 and 2, or it can be such as shown later in FIGS. 7 or 8. Other variants are also well known to skilled in arts. FIGS. 3, 4, and 5 show a combination of a passive and an active mixing means comprising multiple stacked cones 6 secured to a central pipe 2 by gussets 12. There are openings 14 between the upper end of the cone in sectors 16 and the central pipe, and openings 15 in the central pipe within sectors 17. Sectors 16 and 17 are separated by gussets 12. A working gaslift gas is fed in the central pipe via line 23. In operation, digestion gases are formed in the entire volume of the anaerobic stage and form floating bubbles. Bubbles are collected under the cones and produce rotational mixing pattern around cones through openings 14 as shown by arrows. A portion of the gases in sections 17 is directed through openings 15 into the central pipe and serve as a gaslift gas. All these gases eventually are collected in the gas section 52 and evacuated via line 11. The working gas fed via line 23, preferably methane, or possibly oxygen, creates a controllable gaslift effect in the central pipe. As already described, oxygen in very deep tanks can be dissolved virtually completely. Accordingly, the gas collected in section 52 will not contain oxygen.

Figure 6:
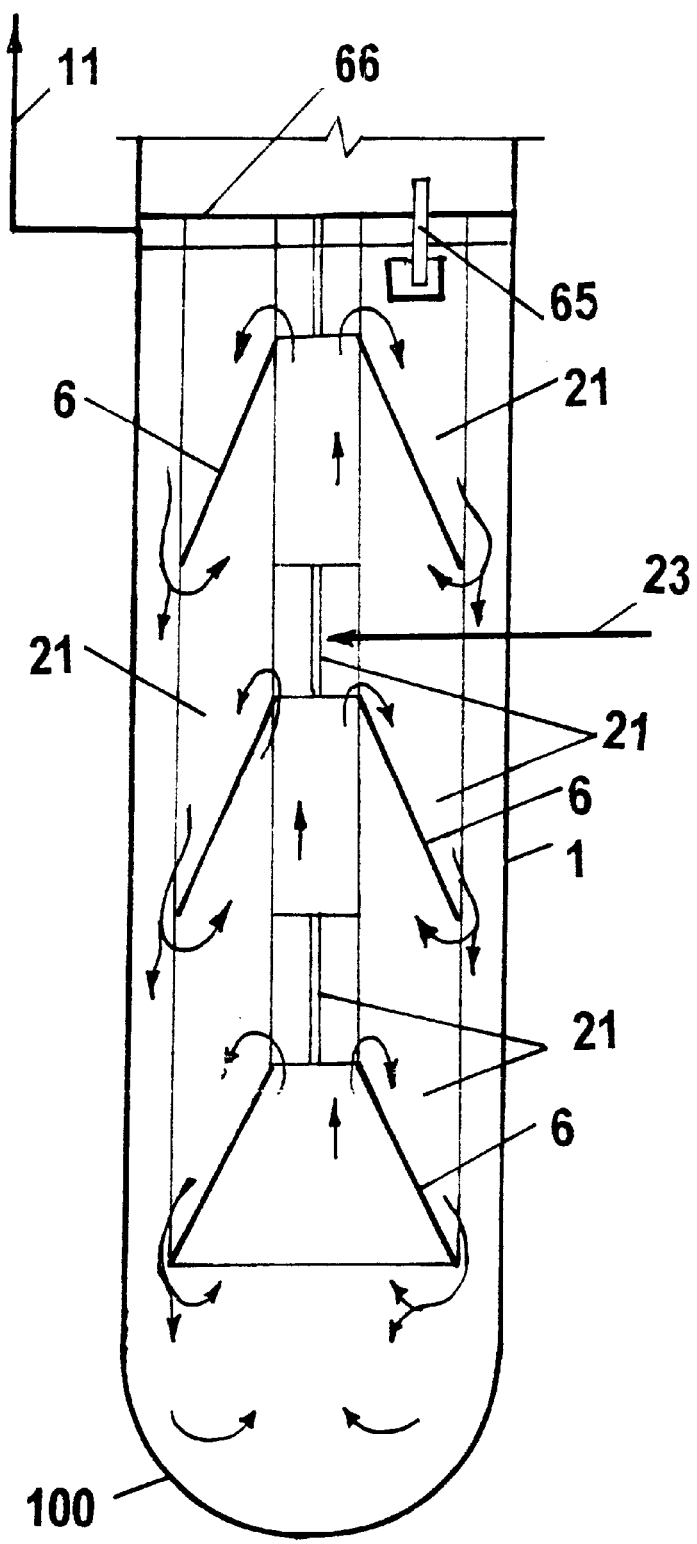
FIG. 6 is a bottom section of anaerobic reactor showing a passive means for sludge or fluidized bed mixing and active means in form of a nonconfined gaslift with complete absoption of the driving gas.

Referring now to FIG. 6, there is shown an anaerobic stage of the reactor 1 from the bottom 100 to the partition 66. FIG. 6 differs from FIG. 3 by the absence of the central pipe in the mixing arrangement. Instead the cones 6 and the connecting gussets 21 form a cage with a central passage into which a working gas is provided via line 23. Hydraulically, the non-confined central passage plays the same role as the central pipe 2 in FIGS. 3, 4, and 5. The operation of the embodiments of FIG. 6 and FIGS. 3, 4, and 5 are similar.

Figure 7:
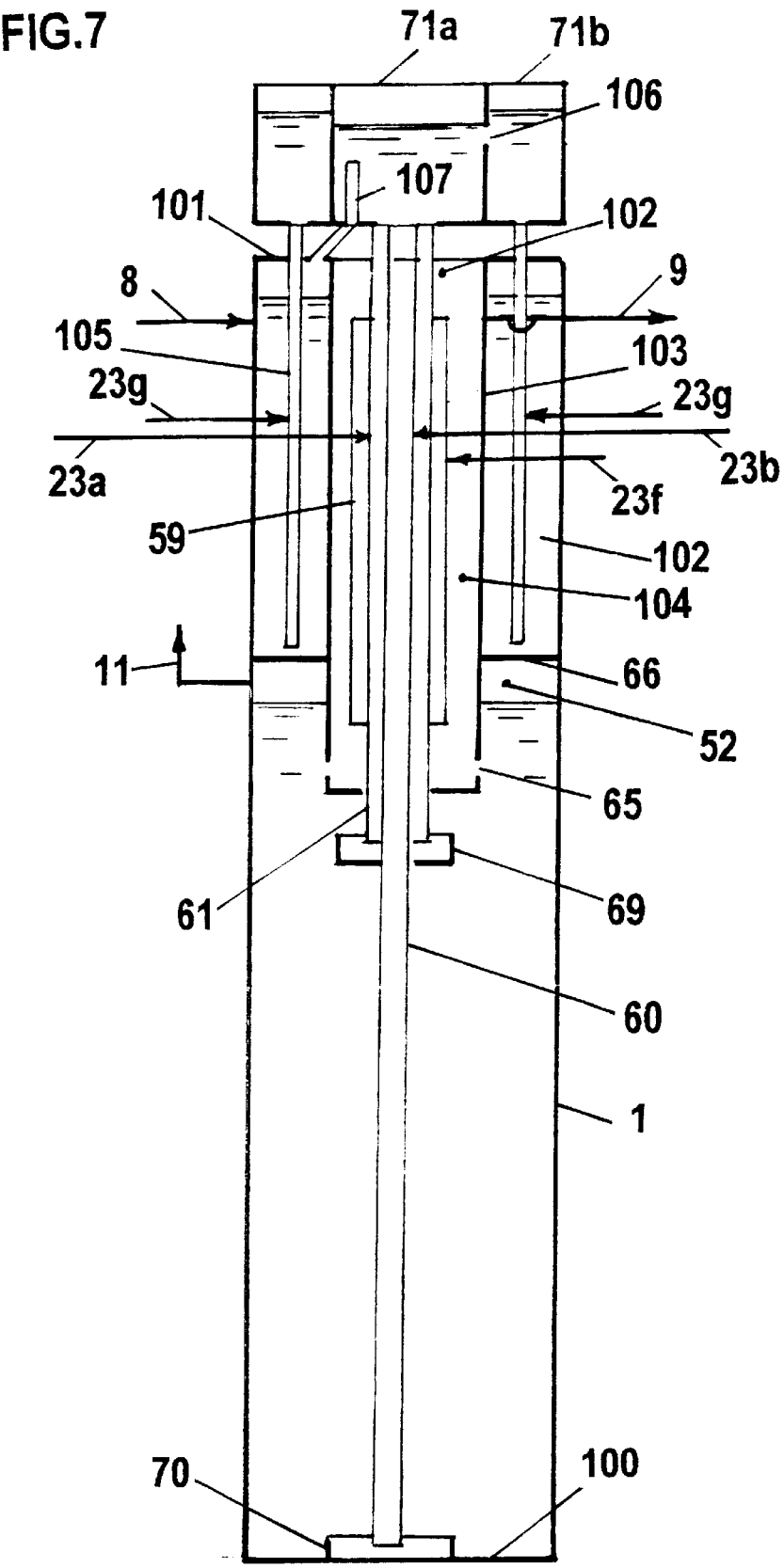
FIG. 7 is a system with a first anaerobic stage and an aerated stage stacked on top of the second anaerobic stage.

Referring now to FIG. 7, there is shown a reactor 1 having a bottom 100, a top 101, and a partition 66, the partition divides the reactor into stacked lower and upper stages. The lower stage of the present embodiment has like elements marked with like numerals already described in previous Figures. Note, the airlift vessel in FIG. 7 is marked as 71a. The portion of the upper level circumscribed by the partition 66, top 101, outer wall of the reactor 1, and a vertical circular partition 103 accommodates a first anaerobic stage 102. Partition 103 delimits the aerated stage within the upper level. This partition can be level with the horizontal partition 66, or, as shown in FIG. 7, it may form a recess in the partition 66, or skilled in art may choose other configurations, for example, the entire upper stage may be the first anaerobic stage, or the anaerobic stage may be inscribed into aerated stage. Alternatively, the upper level stage can be an equalization basin or can include an equalization basin. The first anaerobic stage is equipped with gaslifts 105 supplied with the working gas, air or oxygen, via lines 23*g*. These gaslifts lift mixed liquor from the stage 102 into a separate lift vessel 71*b*, carbon dioxide is partially stripped from the mixed liquor, preferably by air, and returned via the same airlifts back into the first anaerobic stage. Stripping means are not shown in FIG. 8. Gas accumulating at the top of stage 102, mainly carbon dioxide, is released via line 107, preferably in the vessel 71*a* where it is scrubbed and re-stripped from the mixed liquor. A portion of the flow lifted to the vessel 71*b* is transferred via passage 106 into vessel 71*a* and further into the lower anaerobic stage, which in this embodiment is the second anaerobic stage. The effluent from the second anaerobic stage is transferred to the aerated stage via passages 65. The aerated stage can be similar to those already described. The biological transformations in the first anaerobic stage are preferably limited to hydrolysis and acidification of wastes without or with negligible methane production. The second stage can be a methanogenic stage. In general, these two stages can be operated as a two-stage anaerobic process or as a two-phase anaerobic process. The system of FIG. 7 can be provided with any known means for solid-liquid separation, including those shown herein in other Figures.

Figure 8:
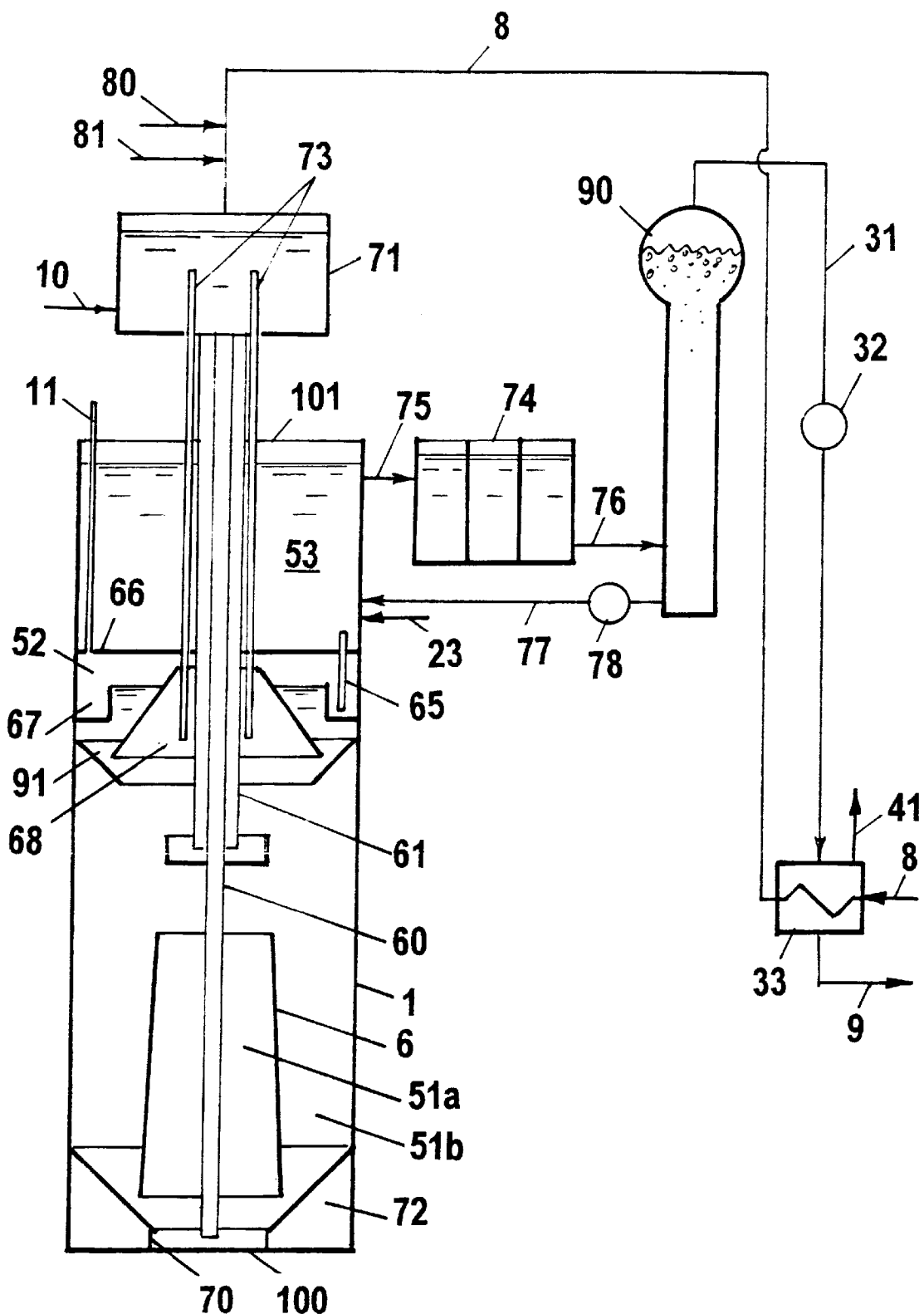
FIG. 8 is a stacked reactor with passive and active mixing means, pressurized gas collection, and a vaporization-steam-recompression-heat utilization system for separating effluent from the mixed liquor in the reactor.

Referring now to FIG. 8, there is shown a biological reactor 1 having a lower portion from the bottom 100 to the partition 66 occupied by an anaerobic stage, and an upper part from the partition 66 to the top 101 used for aerated process stage 53. The anaerobic process stage of FIG. 8 is similar to that of FIG. 1 and the like parts having like numbers will not be described again. FIG. 8 shows a further development of mixing arrangement at the bottom, comprising flow directors 70 and the bottom fill 72 for improved circulation of the fluidized bed or of a viscous sludges. In the upper part of the anaerobic stage, conical baffles 68 and 90 and a water collection through 67 form a gravity separator (settler, or clarifier) for solid-liquid separation. Additional downcomers 73 from the elevated vessel 71 to the vicinity of the anaerobic clarifier are provided for bringing carbonates for neutralization of carbon dioxide in the upper portion of the anaerobic reactor thus eliminating gassing and floatation of the sludge in the clarifier. The aerated stage can be the same as previously described. A system for separating effluent from the mixed liquor includes a stripper 74 for carbon dioxide connected by line 75 to the aerobic stage 53 and further by line 76 to a vacuum-evaporator vessel 90 connected via line 31 to a vacuum-compressor 32 which further is connected to a heat exchanger 33 having an effluent line 9. A heat exchanger is provided with a gas separation line 41. Alternative arrangements for gas separation are also known to skilled in art. Influent line 8 is also connected to the heat exchanger. Alternatively, a recycle line with a pump for heating the contents of either anaerobic stage or the aerated stage in the heat exchanger 33 can also be provided. A portion of the contents of the vacuum-evaporator vessel 90 can be recycled back in the reactor 1, for example, in aerated stage by pump 78 via line 77. In the stripper 74, carbon dioxide is largely removed from the mixed liquor by, preferably, air stripping, although other gases can also be used. In the vacuum-evaporator vessel 90 a portion of the water is evaporated from the mixed liquor. Vacuum improves evaporation at below-boiling point temperature, for example, at a thermophylic biological range of 45 to 75° C. Other temperature ranges can also be used. Vacuum is created by the vacuum-compressor 32 and the steam condensation in a heat exchanger 33. Recompression of the vapors with the vacuum-compressor insures the evacuation of gases which cannot be condensed in the heat exchanger 33 and provides some additional energy to the steam, thus compensating heat losses in the system. The gases to be evacuated are primarily carbon dioxide and traces of methane, oxygen, nitrogen, and possibly other gases. Steam condensation and dissolution of these gases in the cooled, and even in the chilled, condensate will not be sufficient to evacuate gases and to eliminate the "vacuum breakage" due to the gas build up in the vessel 90. Removal of carbon dioxide and reduction or prevention of its formation in the vessel 90 are improved by providing additional alkalinity. Alkalinity can be in a well soluble form, for example, as sodium hydroxide, or in form of soluble/insoluble compounds such as calcium bicarbonates/carbonates. With biomass present, calcium carbonate precipitates into the biomass.

Figure 9:
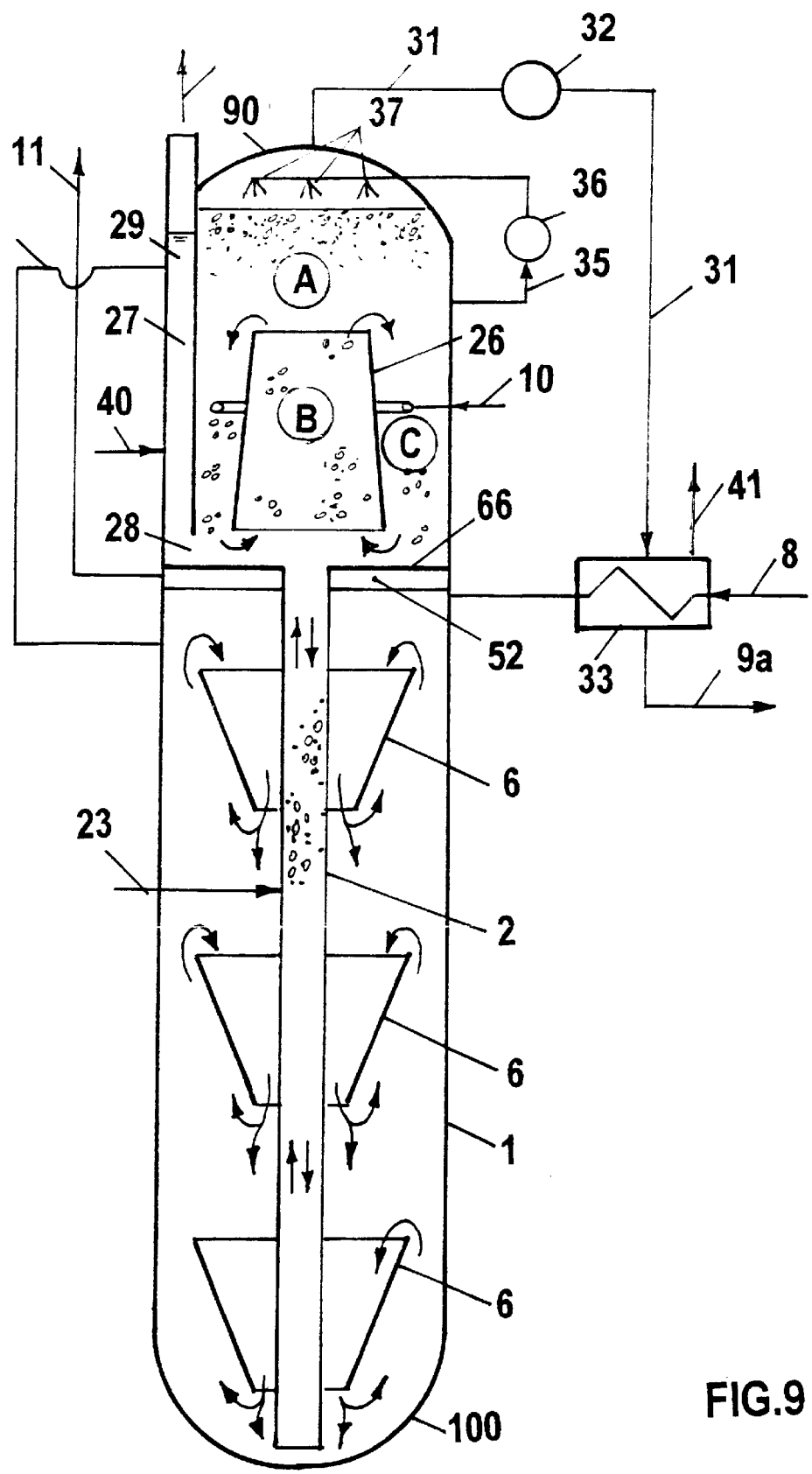
FIG. 9 is an alternative embodiment of that shown in FIG. 8

Referring now to FIG. 9, there is shown a modification of the embodiment exemplified in FIG. 8 with the principal difference in the arrangement of the vaporization vessel 90, which is disposed above the top of the reactor 1 now. This arrangement also includes a recycle line 35 with pump 36 and sprinklers 37 for improving the steam vaporization and for controlling foam in the vessel 90. A carbon dioxide stripping section 27 communicating with the aerated stage via openings 28 and 29 and having air supply 40 and the gas exhaust 30 is provided. The airlift effect in section 27 allows to recycle the degassed contents of the combined aerated section-evaporator vessel-and stripping section to be partially recycled via line 38 in the lower anaerobic stage of the reactor 1. The aerated stage is provided with a conical partition to illustrate the possibility of using it for airlift-aerator: the air, or in this case highly preferably oxygen, is fed via line and a distributor 10 in the downcomer space "C" and is circulating through the riser space "B" with a portion of the liquid being split in the vaporization space "A". The use of oxygen is preferred considering the possibility of its virtually complete utilization so that no aeration gases, for example, nitrogen of air, are vacuum-stripped with vapor in the vessel 90. When the system with addition of alkali is used, it is possible to keep the carbonic acid species in the forms of mainly carbonates and bicarbonates with very little free carbon dioxide. This is achieved by stripping carbon dioxide in section 27 in the presence of elevated alkalinity. Accordingly, there is a very low partial pressure of either carbon dioxide or oxygen, or other gas in the vacuum-vaporization vessel 90. Respectively, a small and low-power vacuum-compressor 32 is needed and a small and simple means for separating gases after the steam condensation are required. FIG. 8 also illustrates the possibility of using the vacuum in the upper stage for mixing the lower stage: vacuum "pulls up" the liquid into vessel 90, when vacuum in vessel 90 is temporarily released the pulled-up liquid rushes thorough the riser-downcomer into the bottom 100 thus producing mixing in the anaerobic stage, afterwards, the liquid is pulled up again. Means for releasing vacuum in vessel 90 are trivial and are not shown. The anaerobic stage is also provided with an active airlift operated with a working gas, preferably oxygen, fed via line 23. The anaerobic stage is further provided with passive mixing cones 6 attached to a central pipe 2 with gussets. In this embodiment, the mixing cones are inverted.

I claim:

1. A method of biological treatment of wastewater with biomass, said wastewater and said biomass form mixed liquor, in a tall reactor, said reactor having a top, a bottom, and an essentially horizontal partition between said top and said bottom, comprising (a) at least one anaerobic treatment step conducted between said bottom and said partition, a digestion gas comprising methane and carbon dioxide is formed in said anaerobic treatment, (b) a step of mixing said mixed liquor in said anaerobic step by at least one controllable gaslift with a gas other than said digestion gas, and (c) at least one step of treatment of said wastewater conducted between said partition and said top of said reactor.

2. The method of claim 1, wherein said at least one controllable gaslift lifts said mixed liquor from at least one location between said bottom and said partition to the uppermost point of said controllable gaslift and returns said mixed liquor in said anaerobic treatment step, whereby said lifting and said returning constitute a lifting-returning operation step effecting said mixing.

3. The method of claim 2, wherein said lifting-returning operation step is selected from a group consisting of non-reversible flow, reversible flow, continuous flow, discontinuous flow, flow through a riser-downcomer pipe, flow through a system of stacked contracting-expanding zones, periodic flow, and combinations thereof.

4. The method of claim 1, wherein said gas other than said digestion gas is selected from the group consisting of an oxidizing gas, oxygen, air, oxides of nitrogen, nitrogen, and combinations thereof.

5. The method of claim 4, wherein said oxidizing gas provides oxidizing reactions in said mixed liquor, whereby said mixed liquor is heated, said oxidizing reactions are selected from biological reactions, abiotic reactions, and combinations thereof.

6. The method of claim 1, wherein a step of stripping said carbon dioxide from said mixed liquor in said anaerobic treatment step is provided, said step of stripping carbon dioxide is selected from a group consisting of gas stripping, oxygen stripping, air stripping, nitrogen stripping, steam stripping, vacuum-stripping, vacuum-vapor-stripping, vacuum-vapor-stripping with steam recompression and condensation, vacuum-vapor-stripping with steam recompression and condensation with preheating the influent, vacuum-vapor-stripping with steam recompression and condensation with heating the contents of said reactor, heat degassing, and combinations thereof.

7. The method of claim 1 and further providing steps of vaporization of wastewater from said mixed liquor with low pressure steam production and condensation of said steam.

8. The method of claim 7, wherein said step of vaporization is selected from a group consisting of vaporization by preheating said mixed liquor, vaporization by vacuuming said mixed liquor, vaporization by vacuuming said mixed liquor with steam recompression and condensation, vaporization by vacuuming said mixed liquor with steam recompression and condensation and preheating said influent, vaporization by vacuuming said mixed liquor with steam recompression and condensation and preheating said mixed liquor, and combinations thereof.

9. The method of claim 1 and further providing steps of feeding reagents selected from a group of recuperable alkalinic species, recuperable oxidation-reduction species, alkalies, acids, nutrients, micronutrients, probiotics, and combinations thereof.

10. The method of claim 1 and further providing steps of transferring said mixed liquor between said step (a) and said step (c).

11. The method of claim 1, wherein said at least one step of treatment of said wastewater conducted between said partition an said top of the reactor is selected from the group consisting of aerobic treatment, aerobic treatment with aeration by air, aerobic treatment with aeration by oxygen, aerobic treatment with nitrification, aerobic treatment with denitrification, aerobic treatment with phosphorus removal, anoxic treatment, treatment with iron as intermediate oxidation-reduction specie, anaerobic hydrolysis treatment, anaerobic acetogenic treatment, anaerobic acidogenic treatment, anaerobic sulfate reduction treatment, anaerobic methanogenic treatmentg, and combinations thereof.

12. The method of claim 1 wherein said reactor is selected from the group of deep shaft reactors, tall above ground reactors, multi-cell reactors, and combinations thereof.

13. The method of claim 1, wherein said partition is a flow-through means capable of collecting said digestion gas and passing through said mixed liquor.

14. A method of biological treatment of wastewater with biomass, said wastewater and said biomass form mixed liquor, in a tall reactor, said reactor having a top, a bottom, and an essentially horizontal partition between said top and said bottom, comprising (a) at least one anaerobic treatment step conducted between said bottom and said partition, a digestion gas comprising methane and carbon dioxide is formed in said anaerobic treatment, (c) at least one step of treatment of said wastewater conducted between said partition and said top of said reactor, and (c) collecting said digestion gas under said partition, whereby said collected gas is pressurized.

15. The method of claim 14, wherein a step of stripping said carbon dioxide from said mixed liquor in said anaerobic treatment step is provided, said step of stripping carbon dioxide is selected from a group consisting of gas stripping, oxygen stripping, air stripping, nitrogen stripping, steam stripping, vacuum-stripping, vacuum-vapor-stripping, vacuum-vapor-stripping with steam recompression and condensation, vacuum-vapor-stripping with steam recompression and condensation with preheating the influent, vacuum-vapor-stripping with steam recompression and condensation with heating the contents of said reactor, heat degassing, and combinations thereof, whereby a methane-rich digestion gas is separated and collected under said partition.

16. A method of biological treatment of wastewater with biomass, said wastewater and said biomass form mixed liquor, in a tall reactor, said reactor having a top, a bottom, and an essentially horizontal partition between said top and said bottom, comprising (a) at least one anaerobic treatment step conducted between said bottom and said partition, a digestion gas comprising methane and carbon dioxide is formed in said anaerobic treatment, (c) at least one step of treatment conducted between said partition and said top of said reactor, and (d) at least one step of vaporization-separation of liquid from solids in said mixed liquor.

17. The method of claim 16, wherein said step of vaporization is selected from a group consisting of vaporization by preheating said mixed liquor, vaporization by bioheating said mixed liquor, vaporization by vacuuming said mixed liquor, vaporization by vacuuming said mixed liquor with steam recompression and condensation, vaporization by vacuuming said mixed liquor with steam recompression and condensation and preheating said influent, vaporization by vacuuming said mixed liquor with steam recompression and condensation and preheating said mixed liquor, and combinations thereof.

18. The method of claim 17, wherein said bioheating is provided by oxidizing said organics and said biomass with an oxidizer selected from a group consisting of oxygen of air, oxygen, iron as intermediate oxidation-reduction specie, and combinations thereof.

19. The method of claim 17 and further providing a step of vacuum evacuation of said digestion gases from said mixed liquor simultaneously with step (d).

20. The method of claim 19, wherein said step of vacuum evacuation is selected from the group consisting of chemical vacuum evacuation, steam recompression vacuum evacuation, and combinations thereof.

* * * * *